(12) United States Patent
Zhang

(10) Patent No.: US 10,929,440 B2
(45) Date of Patent: Feb. 23, 2021

(54) TRADITIONAL CHINESE MEDICINE KNOWLEDGE GRAPH AND ESTABLISHMENT METHOD THEREFOR, AND COMPUTER SYSTEM

(71) Applicant: BOE TECHNOLOGY GROUP CO., LTD., Beijing (CN)

(72) Inventor: Chao Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 105 days.

(21) Appl. No.: 16/313,837

(22) PCT Filed: Mar. 13, 2018

(86) PCT No.: PCT/CN2018/078875
§ 371 (c)(1),
(2) Date: Dec. 27, 2018

(87) PCT Pub. No.: WO2018/205739
PCT Pub. Date: Nov. 15, 2018

(65) Prior Publication Data
US 2019/0171656 A1  Jun. 6, 2019

(30) Foreign Application Priority Data
May 10, 2017 (CN) .......................... 201710326041.3

(51) Int. Cl.
*G06F 16/00* (2019.01)
*G06F 16/28* (2019.01)
(Continued)

(52) U.S. Cl.
CPC .......... *G06F 16/288* (2019.01); *G06F 16/254* (2019.01); *G06F 40/20* (2020.01); *G16H 10/60* (2018.01); *G06F 40/40* (2020.01)

(58) Field of Classification Search
CPC ........ G16H 70/40; G16H 70/60; G16H 10/60; G16H 20/90; G06F 16/288; G06F 16/367; G06F 40/20; G06F 16/254; G06F 40/40
See application file for complete search history.

(56) References Cited

U.S. PATENT DOCUMENTS

| 10,537,600 B2 * | 1/2020 | Zhong ................. A61K 36/074 |
| 2010/0280350 A1 * | 11/2010 | Zhang .................... G16H 50/20 |
| | | 600/407 |

(Continued)

FOREIGN PATENT DOCUMENTS

| CN | 103955531 A | 7/2014 |
| CN | 104318351 A | 1/2015 |

(Continued)

OTHER PUBLICATIONS

Chinese Office Action Office dated May 13, 2019, from application No. 201710326041.3.

(Continued)

*Primary Examiner* — Cheryl Lewis
(74) *Attorney, Agent, or Firm* — Thomas | Horstemeyer LLP

(57) ABSTRACT

A traditional Chinese medicine knowledge graph, a method for establishing a traditional Chinese medicine knowledge graph, and a computer system. The method for establishing the traditional Chinese medicine knowledge graph comprises collecting original data from a traditional Chinese medicine database. The method comprises processing the original data to obtain structural data. The method comprises extracting an entity and an attribute from the structural data. The method comprises constructing the traditional Chinese medicine knowledge graph by utilizing the entity and attribute.

18 Claims, 3 Drawing Sheets

(51) Int. Cl.
    *G06F 40/20*     (2020.01)
    *G16H 10/60*     (2018.01)
    *G06F 16/25*     (2019.01)
    *G06F 40/40*     (2020.01)

(56) References Cited

U.S. PATENT DOCUMENTS

2017/0042495 A1*   2/2017   Matsuzaki ........... G06K 9/6256
2018/0108443 A1    4/2018   Li
2018/0342323 A1*  11/2018   Shankar ................ G06N 7/005

FOREIGN PATENT DOCUMENTS

| | | |
|---|---|---|
| CN | 104462501 A | 3/2015 |
| CN | 104933320 A | 9/2015 |
| CN | 105808931 A | 7/2016 |
| CN | 106021281 A | 10/2016 |
| CN | 106156365 A | 11/2016 |
| CN | 106227820 A | 12/2016 |
| CN | 106570319 A | 4/2017 |
| CN | 103955531 B | 6/2017 |
| CN | 104318351 B | 9/2017 |
| CN | 107169078 A | 9/2017 |
| CN | 104933320 B | 1/2018 |
| WO | WO-2017/185887 A1 | 11/2017 |

OTHER PUBLICATIONS

International Search Report and Written Opinion dated Jun. 12, 2018, from application No. PCT/CN2018/078875.

* cited by examiner

US 10,929,440 B2

TRADITIONAL CHINESE MEDICINE KNOWLEDGE GRAPH AND ESTABLISHMENT METHOD THEREFOR, AND COMPUTER SYSTEM

CROSS REFERENCE

The present application is based upon International Application No. PCT/CN2018/078875, filed on Mar. 13, 2018, which is based upon and claims priority to Chinese Patent Application No. 201710326041.3, filed on May 10, 2017, and the entire contents thereof are incorporated herein by reference.

TECHNICAL FIELD

The present disclosure relates to the field of traditional Chinese medicine (TCM), and more particularly, to a TCM knowledge graph, a method for establishing a TCM knowledge graph, and a computer system.

BACKGROUND

Knowledge graph is a new type of massive knowledge management and service model developed in the era of big data. It is a giant, networked knowledge system built on the structure of "semantic network", which can capture and present the semantic relationship between domain concepts. Internet companies at home and abroad have launched knowledge graphs to improve service quality, such as Google Knowledge Graph, Baidu Knowledge Graph and Sogou's "Knowledge Cube". However, in the field of TCM, there is currently no knowledge graph that can provide similar functions.

It should be noted that, information disclosed in the above background portion is provided only for better understanding of the background of the present disclosure, and thus it may contain information that does not form the prior art known by those ordinary skilled in the art.

SUMMARY

Aspects of the present disclosure provide a TCM knowledge graph, a method for establishing a TCM knowledge graph, and a computer system.

According to one aspect, the present disclosure provides a method for establishing a TCM knowledge graph. The method includes collecting raw data from a TCM database. The method includes processing the raw data to obtain structured data. The method includes extracting entities and attributes between pairs of the entities from the structured data. The method includes constructing the TCM knowledge graph using the entities and attributes.

Optionally, the entities include a number of items of interest or respective values of the items, and the attributes include a relationship between the entities.

Optionally, the entities include one or more of a Chinese medicine name, a disease type, a processing method, a dosage form, a medicinal property, and a drug amount.

Optionally, the attributes include one or more of an influence relationship, a correlation relationship, a dependency relationship and a value relationship.

Optionally, the influence relationship represents an influence between the entities. The correlation relationship is determined based on a number of co-occurrences of the entities in the TCM database. The dependency relationship represents that one of the entities belongs to another one of the entities. The value relationship represents that one of the entities is a value of another one of the entities.

Optionally, the influence relationship includes one or more of curing, restraining, and requiring.

Optionally, the value of the item includes an absolute quantity value of the item, a relative quantity value of the value and a nature of the item.

Optionally, the TCM database includes one or more of a case of an illness database, a TCM journal database, a TCM patent database, and a TCM professional dictionary.

Optionally, processing the raw data to obtain structured data includes processing the raw data using a natural language processing technique.

According to another aspect, the present disclosure provides a TCM knowledge graph. The TCM knowledge graph includes entities obtained from a TCM database, and attributes between pairs of the entities obtained from the TCM database. The entities and the attributes are extracted respectively from structured data generated by processing data collected from the TCM database.

According to another aspect, the present disclosure provides a computer system. The computer system includes a processor, and a memory storing computer readable instructions. When the computer readable instructions stored in the memory are executed, the computer system is caused to perform the method for establishing a TCM knowledge graph according to arrangements of the present disclosure.

It is to be understood that both the foregoing general description and the following detailed description are exemplary and explanatory only and are not restrictive of the present disclosure, as claimed.

This section provides a summary of various implementations or examples of the technology described in the disclosure, and is not a comprehensive disclosure of the full scope or all features of the disclosed technology.

BRIEF DESCRIPTION OF THE DRAWINGS

The accompanying drawings are enclosed to provide a further understanding of the present disclosure and constitute a part of the specification, and together with the following detailed description, to serve for explanation of the present disclosure. But the accompanying drawings are not to be construed as limiting the present disclosure. In the drawings.

DETAILED DESCRIPTION

Hereinafter, the TCM knowledge graph, the method for establishing a TCM knowledge graph, and the computer system according to the present disclosure will be described in further detail with reference to the accompanying drawings and particular arrangements of the present disclosure, such that those skilled in the art may have a better understanding of technical solutions of the present disclosure.

Figure 1:
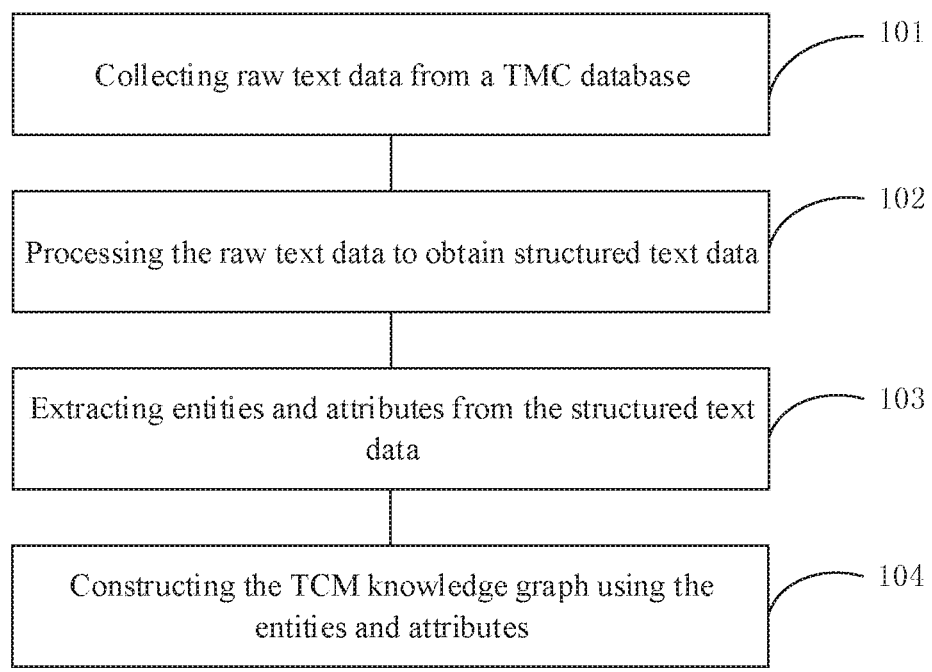
FIG. 1 is a flowchart of the method for establishing a TCM knowledge graph according to an arrangement of the present disclosure.

FIG. 1 is a flowchart of the method for establishing a TCM knowledge graph according to an arrangement of the present disclosure. Referring to FIG. 1, the method for establishing the TCM knowledge graph according to an arrangement of the present disclosure includes the blocks as follows.

In block 101, raw data is collected from a TCM database. In the present arrangement, a computer system can be used to collect raw data from the TCM database. For example, a corresponding database can be accessed via the Internet to collect data from the TCM database. However, the present disclosure is not limited thereto, and the corresponding database may also be accessed through a local area network, a storage medium, or the like, to collect data from the TCM database.

In the present arrangement, the collected raw data may be text data, but the present disclosure is not limited thereto. Other forms of data, such as image data, video data, audio data, etc., can also be acquired. Hereinafter, the disclosure will be explained in more detail with text data as an example, however those skilled in the art will appreciate that other forms of data may also be processed in a similar manner.

In one arrangement, for example, the TCM database may include a case of illness database, a TCM journal database, a TCM patent database, a TCM professional dictionary, or the like.

In block 102, the raw data is processed to obtain structured data. In one arrangement, the raw text data can be processed using natural language processing techniques to generate structured text data using raw text data.

Natural language processing technology is a technology that integrates linguistics, computer science, and mathematics. It can realize effective communication between humans and computers in natural language. At present, various methods for processing text based on natural language processing techniques have been developed in the art. In this arrangement, the use of natural language processing techniques to generate structured text data mainly includes the followings.

Firstly, according to the document structure of the original text data, the paragraph structure is divided to distinguish the paragraphs, authors, recipes, experimental data and other paragraphs, so as to divide the paragraph structure of the original text data. Specifically, the corpus training can be performed by the computer system to form a corpus, the classifier model is constructed according to the corpus, the paragraphs are classified by the classifier model, and the classification prediction result is used as the paragraph attribute.

Then, lexical, grammatical, and/or semantic analysis is performed on the divided paragraph structures to obtain structured text data. Those skilled in the art can provide a specific computer implementation of the above process by constructing various computer systems and providing various computer hardware and software in the light of the methods disclosed in the present disclosure, and thus will not be described herein.

In the field of information technology, information can be classified into two broad categories. A type of information can be represented by data or a unified structure, usually referred to as structured data, such as numbers and symbols; and the other type of information cannot be represented by numbers or a unified structure, such as text, images, sounds, web pages, etc., often referred to as unstructured data. Structured data is a special case of unstructured data. In general, structured data can also be referred to as row data, which can be stored in a database and can be implemented logically using a two-dimensional table structure. Structured data and unstructured data can be understood by those skilled in the art, and thus a more detailed explanation will not be repeated here.

In block 103, entities and attributes between pairs of the entities are extracted from the structured data. For example, in one arrangement, an entity includes an item of interest to the user or the value of the item, and the attribute includes a relationship between the entities. The item of interest to the user may be changed according to the user's attention to the knowledge of TCM. For example, in one example of the present disclosure, a TCM prescription is provided: a traditional Chinese medicine composition for treating lung cancer, consisting of or being made of one or all of the following raw materials in the mass parts: 25-35 parts of raw *Astragalus mongholicus*, 15-25 parts of fried *Codonopsis*, 15-25 parts of *Dioscorea opposita* thunb, 10-20 parts of *Ophiopogon japonicus*, 10-20 parts of *Poria cocos*, 25-35 parts of radix *Codonopsis lanceolatae*, 5-15 parts of *Curcuma zedoary*, 5-15 parts of processed Rhizoma Pinelliae, 10-20 parts of hemsley rockvine root, and 3-7 parts of Schisandra. In this prescription, an item of interest to the user may include individual components of the composition (e.g., individual Chinese medicine names), and may also include the name of the disease (e.g., lung cancer) that the prescription can cure. In addition, the user may also be interested in the value of each component (for example, for the item of *Astragalus mongholicus*, the value is 25-35). Additionally, in this example, the relationships between entities may include "cure," "value," and the like. For example, the relationship between the entity of each traditional Chinese medicine component (e.g., raw *Astragalus mongholicus*, etc.) and the name of the disease (e.g., lung cancer) that can be cure may be "cure". On the other hand, the relationship between the entities of the respective Chinese medicine components (for example, raw *Astragalus mongholicus* and the like) and the amount of the entity (for example, 25-35 parts) may be "value".

Examples of entities and attributes have been described above with reference to a specific example, however those skilled in the art will appreciate that entities and attributes may also include other content depending on the particular TCM data content. For example, the entity may include, but is not limited to, a Chinese medicine name, a disease type, a processing method, a dosage form, a medicinal property, and/or a drug amount. The attributes may include, but are not limited to, influence relationship, correlation relationship, dependency relationship and/or value relationship.

According to an arrangement of the present disclosure, the influence relationship represents an influence between the entities; the correlation relationship is determined based on a number of co-occurrences of the entities in the TCM database; the dependency relationship represents that one of the entities belongs to another one of the entities; and the value relationship represents that one of the entities is a value of another one of the entities.

In further detail, the influence between the entities may include, but not limit to, curing, restraining, and/or requiring. For example, there is an influence of curing between raw *Astragalus mongholicus* and lung cancer, i.e., the raw *Astragalus mongholicus* may be used to cure the lung cancer. In other example, the one drug may approve or go against another. For example, For example, in the Chinese herbal medicine "Compendium of Materia Medica", there are records: "there are seven natural character in medicine, i.e.: those independence do not need to be supplemented by one side; those who are in need of each other are inseparable, such as *ginseng*, licorice, *Astragalus*, rhizoma anemarrhenae, and the like; those of accompany are used in combination; those of dislike may decrease the property of the drug; those of restriction may be restricted by each other; those of contrary may not be used together; and those of mutual detoxication may cause each other poisonous. Therefore, when both entities are names of a TCM drug, the attributes between them may be restraining, requiring, or the like. For example, the relation between the TCM drugs of "the rhizome of Chinese monkshood" and "Pinellia ternata" may be restraining. However, the present disclosure is not limited thereto, and their interaction may be other relationships depending on the specific relationship between the extracted entities.

The correlation relationship is determined based on a number of co-occurrences of the entities in the TCM database. In particular, among the many different TCM prescriptions for treating certain diseases, some of the TCM drugs may appear repeatedly, and the number of times the two TCM drugs appear together in different prescriptions (i.e., the number of co-occurrences) can be used to determine the correlation relationship between two TCM drugs.

The dependency relationship represents that one of the entities belongs to another one of the entities. For example, in a TCM dictionary database, it is described that *Hedyotis diffusa* is a plant of the rubiaceae of the *Hedyotis*. In this arrangement, the extracted entities may include *Hedyotis diffusa*, rubiaceae and *Hedyotis*. In this case, the relationship between the entities may be a dependency relationship, which is represented for example by "belong". For example, the *Hedyotis diffusa* belongs to rubiaceae, the *Hedyotis diffusa* belongs to *Hedyotis*, and rubiaceae belongs to *Hedyotis*.

The value relationship represents that one of the entities is a value of another one of the entities. For example, the relationship between the "raw *Astragalus mongholicus*" and "25-35 parts" may be "value". In this arrangement, the value between the two entities is a relative quantity value (parts), but the present disclosure is not limited thereto. For example, the value between two entities may also be an absolute quantity value, for example, "gram", "qian", etc. are used to indicate the value of the TCM drugs (for example, 25 grams of raw *Astragalus mongholicus* or 5 qian of raw *Astragalus mongholicus*). In other arrangements of the present disclosure, the value relationship is not limited to a particular quantitative "value", but other qualitative results are also included in the value relationship. For example, in other arrangements, the value relationship may also be a property of an entity. For example, in a TCM classic, "*Astragalus mongholicus* has a property of warm and tonic" is described. According to the description, two entities, that is, the TCM drug name "*Astragalus mongholicus*" and the property of "warm and tonic" can be obtained. In this example, although the property of "warm and tonic" is not a numerical value, the relationship between the name of the TCM drug and the medicinal property also belongs to the value relationship.

In block 104, the TCM knowledge graph is constructed using the entities and attributes. In one arrangement, the constructed TCM knowledge graph may include entities and attributes between entities. For example, each entity can be displayed by name or images, and lines between the two entities and the labels on the lines may be used to represent the attributes between the two entities. However, the present disclosure is not limited to the specific implementations of the above-mentioned TCM knowledge graph, and other visualization techniques may be utilized to present various entities and attributes to the user, such as lists, tree diagrams, and the like.

The method for establishing a TCM knowledge graph according to the present disclosure may include collecting raw text data from a TCM database; processing the raw text data to obtain structured text data; extracting entities and attributes from the structured text data; and constructing the TCM knowledge graph using the entities and attributes. Therefore, it is possible to bring together TCM knowledge resources scattered in various databases and literature databases, establish a graph of TCM knowledge, and provide accurate and comprehensive knowledge of TCM for TCM workers and the general public.

Figure 2:
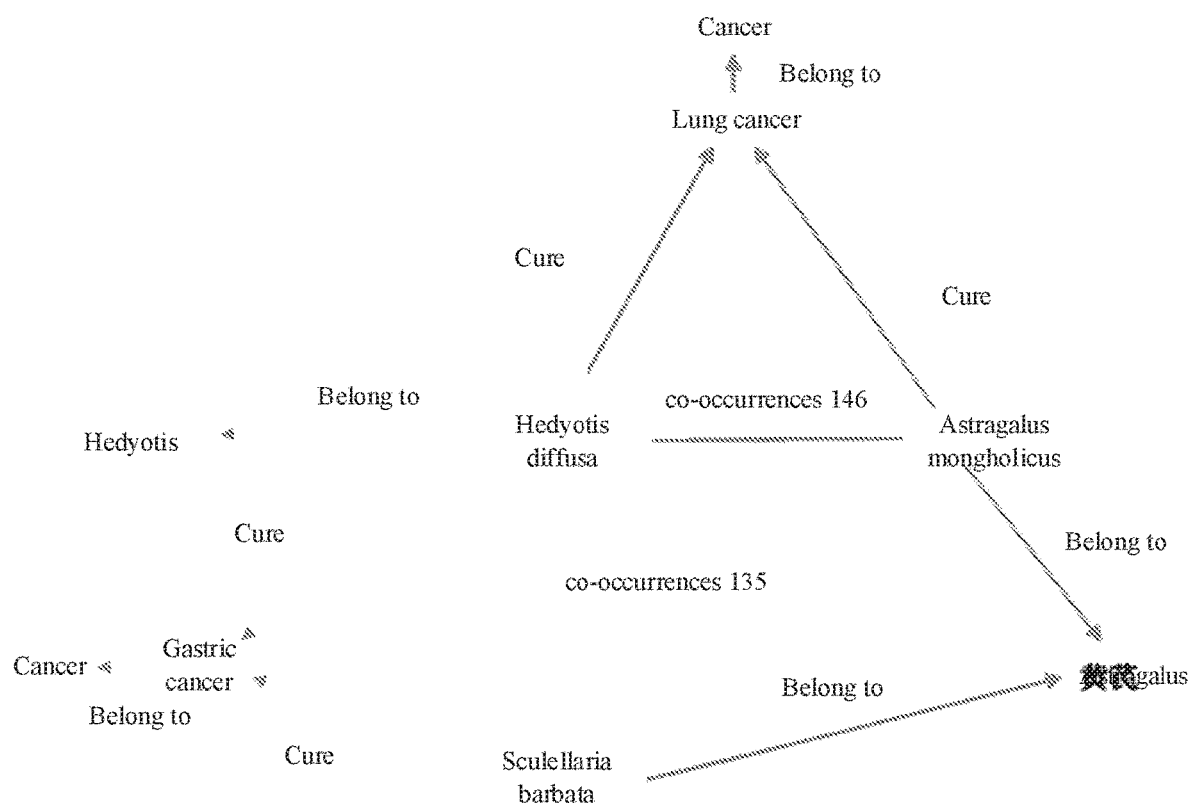
FIG. 2 is a schematic diagram of a TCM knowledge graph according to an arrangement of the present disclosure.

The present disclosure will be described in more detail below with reference to specific arrangements. FIG. 2 is a schematic diagram of a TCM knowledge graph in accordance with an arrangement of the present disclosure. Referring to FIG. 2, a TCM knowledge graph according to the present disclosure includes: entities obtained from a TCM database; and attributes obtained from the TCM database. More specifically, the TCM knowledge graph according to the present disclosure may be constructed using the method according to the foregoing arrangements, for example, the entities and the attributes may be extracted respectively from structured data generated by processing data collected from the TCM database.

For example, referring to FIG. 2, the entities may include a name of the TCM drug, such as *Hedyotis diffusa*, *astragalus mongholicus*, and *Sculellaria barbata*. The entities may include a name of the disease, such as lung cancer and gastric cancer. In addition, the entities may also include other item of interest to the user, such as *Hedyotis*, *astragalus*, cancer, and the like. According to FIG. 2, the attributes may include: cure, such as the relationship between the *Hedyotis diffusa* and the lung cancer, and that between the *Sculellaria barbata* and the gastric cancer; belong, such as the relationship between the *Sculellaria barbata* and the *astragalus*; and correlation, such as *Hedyotis diffusa* and *Astragalus mongholicus* being both useable for curing lung cancer and having a number of co-occurrences of 146, and *Hedyotis diffusa* and *Sculellaria barbata* being both useable for curing gastric cancer and having a number of co-occurrences of 135.

An example of the TCM knowledge graph of the present disclosure has been described in detail with reference to FIG. 2, however, those skilled in the art should understand that the TCM knowledge graph of the present disclosure is not limited to the above content or form, and the TCM knowledge graph may also provide the content of the entities and the attributes to the user in a manner such as a list and a tree graph.

Figure 3:
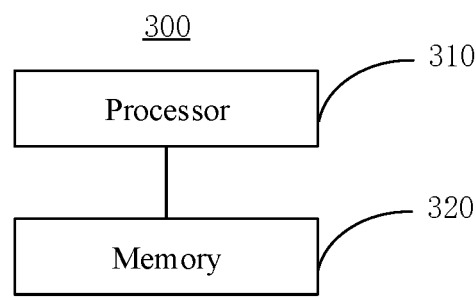
FIG. 3 is a schematic diagram of a computer system according to an arrangement of the present disclosure.

FIG. 3 is a schematic diagram of a computer system according to an arrangement of the present disclosure. Referring to FIG. 3, the computer system 300 according to the present arrangement may include a processor 310 and a memory 320. The memory 320 may store therein with computer readable instructions, which, when being executed, causing the computer system 300 to perform a method for establishing a TCM knowledge graph according to the previous arrangements.

Figure 4:
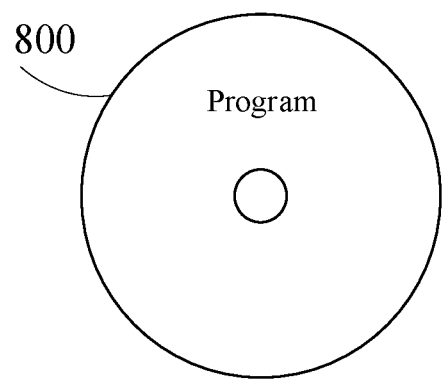
FIG. 4 is a schematic diagram illustrating a program product according to an arrangement of the present disclosure.

With reference to FIG. 4, a program product 800 (e.g., a non-transitory computer readable medium) for implementing the above method according to an arrangement of the present disclosure is described. The program product 800 may employ a portable compact disc read-only memory (CD-ROM) and include program code, and may be executed on a terminal device, such as a personal computer. However, the program product of the present disclosure is not limited thereto, and in this document, the readable storage medium may be any tangible medium that contains or stores program that can be used by or in conjunction with an instruction execution system, apparatus, or device.

The program product may employ any combination of one or more readable medium. The readable medium may be a readable signal medium or a readable storage medium. A readable storage medium may be, but not limited to, for example an electronic, magnetic, optical, electromagnetic, infrared, or semiconductor system, apparatus, or device, or any combination thereof. More specific (non-exhaustive) examples of readable storage medium include: electrical connections with one or more wires, portable disks, hard disks, a random access memory (RAM), a read only memory (ROM), an erasable programmable read-only memory (EPROM or flash memory), an optical fiber, a portable compact disc read-only memory (CD-ROM), an optical storage device, a magnetic storage device, or any suitable combination thereof.

A computer readable signal medium may include a data signal that propagates in baseband or as part of carrier wave, and the data signal carries readable program code. Such propagated data signals may have a variety of forms, including but not limited to electromagnetic signals, optical signals, or any suitable combination of the above. The readable signal medium may also be any readable medium other than a readable storage medium, which can transmit, propagate, or transport a program for use by or in connection with an instruction execution system, apparatus, or device.

The program code embodied on the readable medium may be transmitted using any appropriate medium, including but not limited to wireless, wire, optical fiber cable, RF, or any suitable combination thereof.

Program code for carrying out operations of the present disclosure may be programmed in any combination of one or more programming languages including object-oriented programming languages such as Java, C++, and the like, as well as conventional process-oriented programming languages such as the "C" language or similar programming languages. The program code may be executed entirely on the user's computing device, or partly on the user's device, or the program code may be as a stand-alone software package to be executed, or a part of the program code can be executed on the user's computing device and other part of the program code can be executed on the remote computing device, or the program code may be executed entirely on the remote computing device or server. In situations related to remote computing devices, the remote computing device may be connected to the user computing device through any type of network, including a local area network (LAN) or a wide area network (WAN), or may be connected to an external computing device (e.g., using the internet provided by a network service provider).

According to the TCM knowledge graph, the method for establishing a TCM knowledge graph and the computer system according to the present disclosure, it may include collecting raw text data from a TCM database; processing the raw text data to obtain structured text data; extracting entities and attributes from the structured text data; and constructing the TCM knowledge graph using the entities and attributes. Therefore, it is possible to bring together TCM knowledge resources scattered in various databases and literature databases, establish a graph of TCM knowledge, and provide accurate and comprehensive knowledge of TCM for TCM workers and the general public.

It should be appreciated that, the above arrangements are exemplary implementations for illustrating the principle of the present disclosure only, while the present disclosure is not limited thereto. Various modifications and improvements are possible to those of ordinary skill in the art without departing from the spirit and essence of the present disclosure. All these modifications and improvements will also fall into the protection scope of the present disclosure.

What is claimed is:

1. A method for establishing a medical knowledge graph implemented in a data processing apparatus, the method comprising:
   collecting, by at least one hardware processor of the data processing apparatus, raw data from a medical database;
   processing, by the at least one hardware processor, the raw data to obtain structured data;
   extracting, by the at least one hardware processor, entities and attributes from the structured data; and
   constructing, by the at least one hardware processor, a medical knowledge graph using the entities and attributes, wherein the entities comprise a plurality of items of interest or respective values of the items, the attributes comprise a relationship between the entities, and the entities and attributes are shown in the medical knowledge graph.

2. The method according to claim 1, wherein the entities comprise at least one of: a medicine name, a disease type, a processing method, a dosage form, a medicinal property, and a drug amount.

3. The method according to claim 1, wherein the attributes comprise at least one of: an influence relationship, a correlation relationship, a dependency relationship, and a value relationship.

4. The method according to claim 3, wherein,
   the influence relationship represents an influence between the entities;
   the correlation relationship is determined based on a number of co-occurrences of the entities in the medical database;
   the dependency relationship represents that one of the entities belongs to another one of the entities; and
   the value relationship represents that one of the entities is a value of another one of the entities.

5. The method according to claim 4, wherein the influence relationship comprises at least one of: curing, restraining, and requiring.

6. The method according to claim 1, wherein the value of each item of the entities comprises an absolute quantity value of the item, a relative quantity value of the value, and a nature of the item.

7. The method according to claim 1, wherein the medical database comprises at least one of: a case of an illness database, a medical journal database, a medical patent database, and a medical professional dictionary.

8. The method according to claim 1, wherein processing the raw data to obtain structured data comprises: processing the raw data using a natural language processing technique.

9. The method according to claim 1, wherein the raw data is text data.

10. A non-transitory computer-readable storage medium having program instructions stored thereon that, when executed by at least one hardware processor of a data processing apparatus, causes the data processing apparatus to present a medical knowledge graph comprising:
    entities obtained from a medical database; and
    attributes obtained from the medical database, wherein the entities and the attributes are extracted respectively by the at least one hardware processor from structured data generated by processing data collected from the medical database, wherein the entities comprise a plurality of items of interest or respective values of the items, the attributes comprise a relationship between the entities, and the entities and attributes are shown in the medical knowledge graph.

11. A data processing apparatus, comprising:
at least one hardware processor; and
computer readable instructions stored in a memory and executable by the at least one hardware processor that, when executed by the at least one hardware processor, direct the data processing apparatus to perform a method for establishing a medical knowledge graph, the method comprising:
   collecting raw data from a medical database;
   processing the raw data to obtain structured data;
   extracting entities and attributes from the structured data; and
   constructing the medical knowledge graph using the entities and attributes, wherein the entities comprise a plurality of items of interest or respective values of the items, the attributes comprise a relationship between the entities, and the entities and attributes are shown in the medical knowledge graph.

12. The data processing apparatus according to claim 11, wherein the entities comprises at least one of: a medicine name, a disease type, a processing method, a dosage form, a medicinal property, and a drug amount.

13. The data processing apparatus according to claim 11, wherein the attributes comprises at least one of: an influence relationship, a correlation relationship, a dependency relationship, and a value relationship.

14. The data processing apparatus according to claim 13, wherein,
   the influence relationship represents an influence between the entities;
   the correlation relationship is determined based on a number of co-occurrences of the entities in the medical database;
   the dependency relationship represents that one of the entities belongs to another one of the entities; and
   the value relationship represents that one of the entities is a value of another one of the entities.

15. The data processing apparatus according to claim 14, wherein the influence relationship comprises at least one of: curing, restraining, and requiring.

16. The data processing apparatus according to claim 11, wherein the value of each item of the entities comprises an absolute quantity value of the item, a relative quantity value of the value, or a nature of the item.

17. The data processing apparatus according to claim 11, wherein the medical database comprises at least one of: a case of illness database, a medical journal database, a medical patent database, and a medical professional dictionary.

18. The data processing apparatus according to claim 11, wherein processing the raw data to obtain structured data comprises: processing the raw data using a natural language processing technique.

\* \* \* \* \*